United States Patent [19]

Myers, Jr. et al.

[11] 4,190,610

[45] Feb. 26, 1980

[54] CATALYTIC CODIMERIZATION OF NORBORNADIENE WITH PENTADIENE

[75] Inventors: Harry K. Myers, Jr., Aston; James E. Lyons, Wallingford; Abraham Schneider, Overbrook Hills, all of Pa.

[73] Assignee: Sun Oil Company of Pennsylvania, Philadelphia, Pa.

[21] Appl. No.: 933,228

[22] Filed: Aug. 14, 1978

Related U.S. Application Data

[63] Continuation of Ser. No. 819,441, Jul. 27, 1977, abandoned.

[51] Int. Cl.$^2$ .............................................. C07C 13/32
[52] U.S. Cl. ..................................... 585/361; 585/14; 585/22; 149/120
[58] Field of Search ......... 260/666 A, 666 B, 666 PY

[56] References Cited

U.S. PATENT DOCUMENTS 2,875,256   2/1959   Hyman ............................ 260/666 A

OTHER PUBLICATIONS

Greco et al., J. Org. Chem., 35, No. 1, p. 271, 1970.
Carbonero et al., J. Org. Chem., 36, No. 10, p. 1443, 1971.

*Primary Examiner*—Veronica O'Keefe
*Attorney, Agent, or Firm*—J. Edward Hess; Donald R. Johnson; Anthony Potts, Jr.

[57] ABSTRACT

Catalytic codimerization of norbornadiene and 1,3-pentadiene yields an olefinic codimer which, after hydrogenation, has utility as a high energy missile fuel or a diluent for a higher viscous missile fuel. Used is a three-component homogeneous catalytic system, consisting of cobaltic or cobaltous acetylacetonate, 1,2-bisdiphenylphosphina ethane and an alkyl aluminum chloride.

10 Claims, No Drawings

CATALYTIC CODIMERIZATION OF NORBORNADIENE WITH PENTADIENE

The invention herein described was made in the course of or under a contract thereunder with the United States Air Force Systems Command.

CROSS REFERENCE TO RELATED APPLICATION

This is a continuation of application Ser. No. 819,441, filed July 27, 1977, now abandoned and which the latter is related to U.S. Application Ser. No. 819,444, filed July 27, 1977 by the aforementioned inventors.

BACKGROUND OF THE INVENTION

The invention relates to the catalytic codimerization of norbornadiene and 1,3-pentadiene. Particularly the invention relates to the preparation of an olefinic codimer of norbornadiene and 1,3-pentadiene using a specified catalyst system. Hydrogenation of the olefinic codimer yields a saturated codimer having utility as a high energy fuel or a diluent for such fuels. The pentadiene is referred to hereinafter as PD.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene (I) is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

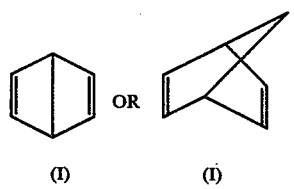

NBD can be easily dimerized to an exo-exo hexacyclic dimer. Thus one problem in reacting NBD with another hydrocarbon reactant is to minimize the formation of the foregoing dimer while encouraging the formation of the desired codimer.

A. Greco et al, in the Journal of Organic Chemistry, Vol. 35, No. 1, Jan. 1970, page 271 in article titled "Catalytic Norbornadiene-Butadiene and Norbornadiene-1,1-Dimethylallene Codimerization" discloses using bis(cyclooctatetraene) iron or $FeCl_3$-$(iC_3H_7)MgCl$ as a catalyst for reacting norbornadiene with 1,3-pentadiene.

SUMMARY OF THE INVENTION

Rapid codimerization of NBD and PD is obtained using a catalytic amount of a three-component homogeneous catalytic system consisting of cobaltic or cobaltous acetylacetonate, 1,2-bisdiphenylphosphino ethane and one of three alkyl aluminum chlorides. The reaction rate is relatively rapid and the selectivity as to the resulting codimer of NBD and PD is good. Resulting codimer can be hydrogenated and then used as a missile fuel.

DESCRIPTION

Cobaltic acetylacetonate $(Co(C_5H_7O_2)_3)$ is referred to hereinafter as $CoA_3$ whereas the cobaltous form is referred to as $CoA_2$ $(Co(C_5H_7O_2)_2)$; collectively the two are referred to as CoA. The 1,2-bisdiphenylphosphino ethane $((C_6H_5)_2PCH_2)_2)$ is referred to as DIPHOS while the alkyl aluminum chloride is referred to as AAC.

The catalytic codimerization of NBD and PD via present invention can be represented by the following formula reaction:

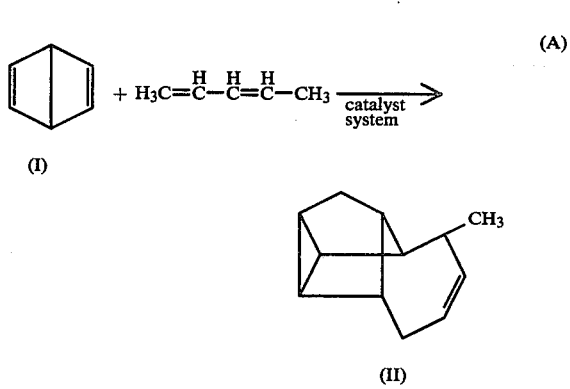

As shown, NBD and PD are contacted in the presence of a catalytic amount of a catalyst system defined herein. Coproducts may also be made.

Olefinic codimer II is a tetracyclic hydrocarbon having the molecular formula $C_{12}H_{16}$ and a C/H molar ratio of 0.750. The codimer may be hydrogenated to form α-methyltetramethylene nortricyclane (III). The hydrogenation of olefinic codimer II can be represented by the following formula reaction:

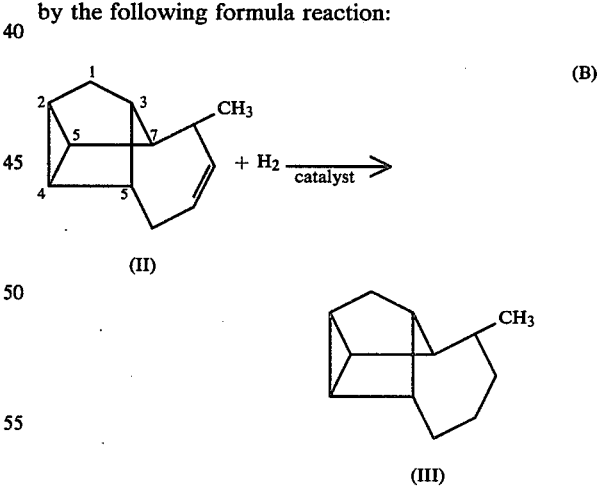

Hydrogenated product III is also a tetracyclic hydrocarbon having the molecular formula $C_{12}H_{18}$ and a C/H molar ratio of 0.667. Product III may be used as a component of a high density missile fuel.

The NBD used can contain a nominal amount of similar hydrocarbons, however, which if present should not be of a type which could adversely effect the reaction. If the NBD used contains undesirable hydrocarbons, they can be removed by known means. The foregoing also applied to the PD used. Thus the hydrocarbons used in the invention can consist essentially of NBD and PD.

In the codimerization of NBD and PD one mole of each reacts with the other to form one mole of the NBD-PD codimer II. However, if the NBD to PD mole ratio is too large homodimerization can occur with an adverse effect on codimer yields. On the other hand, if the NBD to PD mole ratio is too low then the yield per pass can be too low and hence uneconomical. Within the aforementioned limits a preferred NBD to PD mole ratio is in the range between from about 0.01 to about 10 with about 0.1 to about 4 more preferred.

The catalytic system favoring the aforementioned codimerization reaction (A) contains three components. All three components of the catalyst system are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to as DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system.

The amount of the CoA present should be catalytically sufficient to obtain the desired product. Generally the NBD to CoA mole ratio can range between from about 10 to about 2000 with a preferred range between from about 20 to about 1000.

The second component of the catalyst system is DIPHOS. The amount of this second component of the catalyst system should be catalytically sufficient to obtain the desired product. Generally the DIPHOS to CoA mole ratio can range between from about 0.1 to about 5 with a preferred range between from about 0.25 to about 4.

DEAC, EADC or EASC is the third component of the catalyst system with DEAC preferred. The amount of the third component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed hereinafter while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, cyclopentane, diethylether, chlorobenzene, bromobenzene, chlorinated cyclohexane and the like. As to the amount of solvent used, excessive amounts decrease the reaction rate, and thus adversely affect the economics for a commercial operation. All three components are commercially available and methods for their preparation are well known.

The codimerization of NBD and PD with the three-component catalyst system can occur at ambient temperature. Thus the temperature of the homogeneous feed catalyst system mixture need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally, however, the codimerization of NBD and PD with a reasonable amount of the three-component catalyst system is not characterized by an extremely rapid exotherm.

Selective codimerization of the NBD and PD most efficiently occurs in a liquid phase and therefore it is not desirable to have the reaction temperature largely exceed the boiling points of the NBD and/or any solvent. Conversely, if the temperature is too low the reaction may be too slow to be economically feasible. An operable temperature range is between from about 20° C. to about 100° C. with about 25° C. to about 85° C. a preferred range. The operating pressure can vary substantially, however, it can range from about atmospheric up to about 2000 psi with about 1000 psi a preferred upper value. Process economics favor lower operating pressure, however, a moderately elevated reaction pressure may be desirable to keep the PD in solution.

To further illustrate the invention the following example is provided along with comparative ones.

EXAMPLE

Into a Fisher-Porter reaction vessel were added 6.5 milligrams (0.018 millimoles) of $CoA_3$, 25.7 milligrams (0.064 millimoles) of DIPHOS, 0.50 milliliters of chlorobenzene, 0.50 millilites (4.9 millimoles) of NBD and 1.0 milliliters (10 millimoles) of PD. The combined materials were mixed and deaerated at 24° C. under nitrogen. Then to the deaerated mixture was added 0.74 millimoles of a 1.9 molar solution of DEAC in toluene. A slight exotherm occurred with the temperature reaching 35° C. after the addition of the DEAC. After a total of 58 minutes the reaction mixture was treated with isopropyl alcohol to quench the catalyst. After separation a portion of the hydrocarbon product was analyzed by vapor phase chromatographic analysis.

The analysis indicated that 30.3% of the NBD was converted and that selectivity to codimer was 88.5%. The amount of PD converted was 11.8%.

Analogous results will be obtained when $CoA_2$ is used in lieu of $CoA_3$ and/or the DEAC is replaced by EADC or EASC.

Hydrogenation of codimer II to hydrogenated product III via reaction B, can be readily achieved by using a hydrogenation catalyst such as $PtO_2$. The temperature of hydrogenation can vary widely, however, generally it will be between ambient and about 100°–200° C. The hydrogen pressure can vary substantially.

An attempt was unsuccessful to prepare codimer II using the following catalyst systems: ferric acetylacetonate-DIPHOS-DEAC or triphenylphosphine-cobaltous carbonyl-DEAC.

The invention claimed is:

1. Process for the catalytic and codimerization of norbornadiene with 1,3-pentadiene comprising:
   (a) contacting norbornadiene and 1,3-pentadiene in the presence of a catalytic amount of a three-component homogeneous catalytic system consisting of cobaltic or cobaltous acetylacetonate, 1,2-bisdiphenylphosphino ethane and an alkyl aluminum chloride selected from the group consisting of diethylaluminum chloride, ethyl aluminum dichloride and ethyl aluminum sesquichloride;
   (b) having the contacting occurring at a temperature within the range from between about 20° C. to about 100° C. and
   (c) continuing the contacting until the 1,3-pentadiene-norbornadiene codimer is prepared.

2. Process according to claim 1 wherein the bisdiphenylphosphino ethane to the acetylacetonate mole ratio is in the range between from about 0.1 to about 5.

3. Process according to claim 1 wherein the norbornadiene to the 1,3-pentadiene mole ratio is in the range between from about 0.01 to about 10.

4. Process according to claim 1 wherein the alkyl aluminum chloride to the acetylacetonate mole ratio is in the range between from about 0.5 to about 100.

5. Process according to claim 1 wherein the norbornadiene to the acetylacetonate mole ratio is in the range between from about 10 to about 2000.

6. Process according to claim 5 wherein an inert solvent is present.

7. Process according to claim 6 wherein the inert solvent is selected from the group consisting of aromatic hydrocarbon, cycloparaffin, ether, halogenated aromatic, halogenated paraffin and halogenated cycloparaffin.

8. Process according to claim 7 wherein the bisdiphenylphosphino ethane to the acetylacetonate mole ratio is in the range between from about 0.1 to about 5.

9. Process according to claim 8 wherein the norbornadiene to the 1,3-pentadiene mole ratio is in the range between from about 0.01 to about 10.

10. Process according to claim 9 wherein the alkyl aluminum chloride to the acetylacetonate mole ratio is in the range between from about 0.5 to about 100.

* * * * *